(12) United States Patent
Walter et al.

(10) Patent No.: US 8,475,469 B2
(45) Date of Patent: Jul. 2, 2013

(54) MEDICAL INSTRUMENT FOR MANIPULATION OF AN UTERUS

(75) Inventors: Christian Walter, Emmingen (DE); Jacques Donnez, Brussels (BE)

(73) Assignee: Karl Storz GmbH & Co. KG (DE)

( * ) Notice: Subject to any disclaimer, the term of this patent is extended or adjusted under 35 U.S.C. 154(b) by 281 days.

(21) Appl. No.: 12/271,466

(22) Filed: Nov. 14, 2008

(65) Prior Publication Data

US 2009/0131954 A1 May 21, 2009

(30) Foreign Application Priority Data

Nov. 16, 2007 (DE) .......................... 10 2007 056 388

(51) Int. Cl.
*A61B 17/42* (2006.01)

(52) U.S. Cl.
USPC .......................................................... 606/119

(58) Field of Classification Search
USPC ....... 600/227–229, 231–233, 235; 604/96.01, 604/104–109; 606/1, 108, 119, 135–137, 606/193

See application file for complete search history.

(56) References Cited

U.S. PATENT DOCUMENTS

| | | | | |
|---|---|---|---|---|
| 3,096,764 A | * | 7/1963 | Uddenberg | .................... 604/176 |
| 3,878,848 A | * | 4/1975 | Hiebert | .......................... 606/148 |
| 4,807,625 A | * | 2/1989 | Singleton | ...................... 606/125 |
| 5,174,276 A | * | 12/1992 | Crockard | ....................... 600/104 |
| 5,209,754 A | * | 5/1993 | Ahluwalia | ...................... 600/207 |
| 5,259,836 A | * | 11/1993 | Thurmond et al. | ........... 600/431 |
| 6,159,170 A | * | 12/2000 | Borodulin et al. | ............. 601/46 |
| 6,651,992 B1 | * | 11/2003 | Smith, Sr. | .................. 280/47.26 |
| 7,334,503 B1 | * | 2/2008 | Newman et al. | ............. 81/53.11 |
| 2003/0187334 A1 | | 10/2003 | Biswas | |
| 2004/0138528 A1 | * | 7/2004 | Richter et al. | ................. 600/134 |
| 2005/0277948 A1 | | 12/2005 | Cedars et al. | |
| 2007/0088351 A1 | * | 4/2007 | Ewaschuk et al. | ............... 606/45 |

FOREIGN PATENT DOCUMENTS

| | | |
|---|---|---|
| DE | 20110921 U1 | 12/2001 |
| DE | 69532474 T2 | 11/2004 |
| DE | 10341561 A1 | 4/2005 |
| EP | 0400458 A1 | 12/1990 |
| EP | 0890342 B1 | 1/1999 |
| WO | 2008074054 A1 | 6/2008 |

OTHER PUBLICATIONS

European Search Report; EP 08 16 9062; Sep. 23, 2009; 5 pages.

* cited by examiner

*Primary Examiner* — Ryan Severson
*Assistant Examiner* — Ashley Cronin
(74) *Attorney, Agent, or Firm* — St. Onge Steward Johnston & Reens LLC

(57) ABSTRACT

A medical instrument has a rod-shaped body which has a distal end section which can be inserted through a vagina into an uterus. A bell-shaped element is mounted on the rod-shaped body. The bell-shaped element being slidingly displaceable along said rod-shaped body at least between an axial position on said rod-shaped body close to a proximal end thereof and up to said distal end section inserted in an uterus.

14 Claims, 6 Drawing Sheets

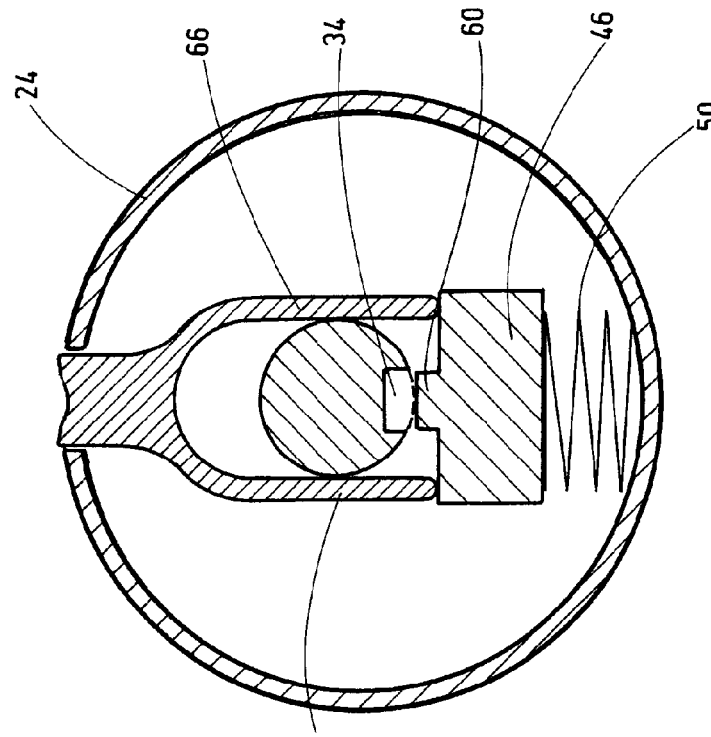
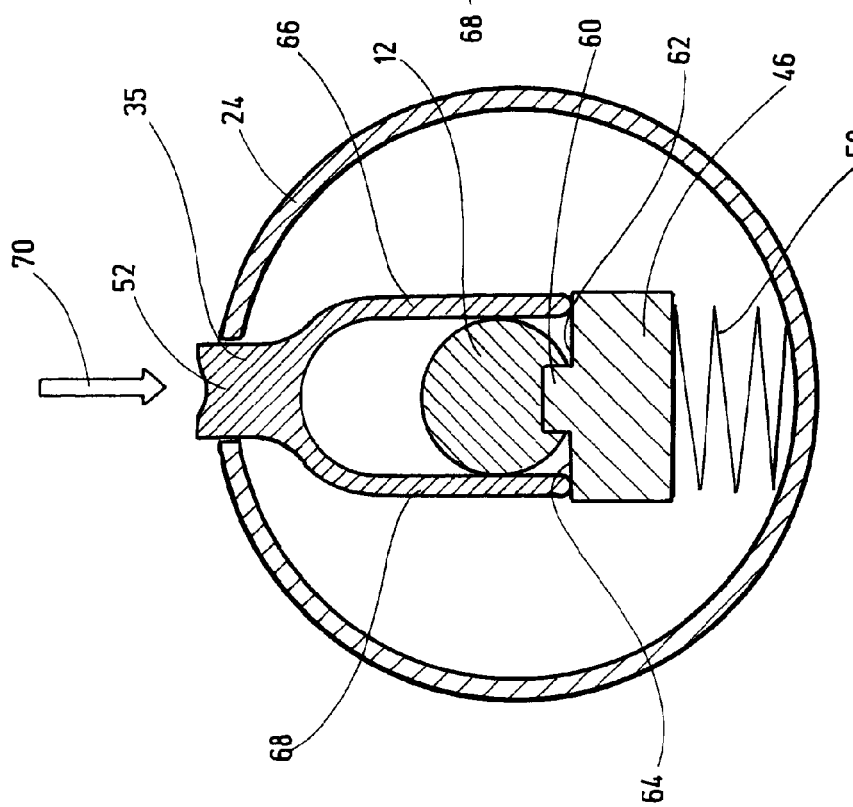

MEDICAL INSTRUMENT FOR MANIPULATION OF AN UTERUS

BACKGROUND OF THE INVENTION

The invention relates to a medical instrument for manipulation of an uterus, with a rod-shaped body whose distal end section can be inserted through the vagina into the uterus, said rod-shaped body carrying a bell-shaped element that can be moved to and fro along the rod-shaped body.

A medical instrument that is used for manipulation of an uterus and that has these design features is known from US 2003/0187334 A1.

Medical instruments of this kind, also called uterus manipulators, are used, among other reasons, to bring the uterus to a desired position for laparoscopic examinations of the lower abdominal region of female patients or in preparation for a surgical intervention. This is done, for example, in order to be able to examine a concealed surface of the uterus or to perform a surgical intervention, for example a hysterectomy (removal of the uterus).

The medical instrument mentioned at the outset has a rectilinear rod, which is provided with a coarse external thread along almost the whole of its length. A bell-shaped element sits on the external thread and can be moved to and fro along the rod by rotation. By means of a relative rotational movement between the bell-shaped element and the rod, the axial position of the bell-shaped element on the rod can be changed. In this relative rotational movement, the bell-shaped element can be held securely by the operator, and the rod is rotated, or the rod is held securely by the operator, and the bell-shaped element is rotated.

To manipulate the uterus, the bell-shaped element is first fitted on the distal end section of the rod. The rod, with the bell-shaped element arranged on its distal end section, is then inserted into the vagina until the bell-shaped element encloses the mouth of the uterus. The bell-shaped element is held securely in this position by the wall of the vagina. The rod provided with the coarse thread is then rotated by the operator such that it is driven into the uterus. With the instrument positioned in this way, the operator is able to manipulate the uterus by moving the rod, in order to perform an examination or a surgical intervention.

A disadvantage of this medical instrument is that the axial position of the bell-shaped element on the rod is changed by a rotational movement between the bell-shaped element and the rod. In order to move the bell-shaped element from a proximal end to a distal end, the operator has to turn either the rod of the bell-shaped element approximately 20 to 25 times. This is awkward, and quite a long time is taken to insert and position the medical instrument in the body of the patient.

A further disadvantage of said instrument is that the bell-shaped element is arranged on the distal end section of the rod when the latter is inserted into the uterus. As a result, the distal end section of the rod is not visible to the operator. He is therefore unable to check the position of the distal end section of the rod that is rotated into the uterus and is therefore also unable to correct it. This can have the effect that a wrongly positioned distal end section of the rod does not move into the cavity of the uterus and is instead driven into the tissue of the uterus, as a result of which the sensitive tissue may be damaged by the coarse thread. The coarse thread poses a danger of tissue areas attaching to it and being rotated with it, with the result that the cervix becomes twisted.

The object of the invention is therefore to further develop a medical instrument of the type mentioned at the outset, in such a way that the insertion and positioning of the instrument in the body of the patient can be performed easily and quickly by the operator and in a manner that causes minimal trauma to the patient.

SUMMARY OF THE INVENTION

According to the invention, this object is achieved by a medical instrument comprising a rod-shaped body having a distal end section which can be inserted through a vagina into an uterus, a bell-shaped element mounted on said rod-shaped body, said bell-shaped element being slidingly displaceable along said rod-shaped body at least between an axial position on said rod-shaped body close to a proximal end thereof and up to said distal end section inserted into an uterus.

The sliding displacement of the bell-shaped element along the rod-shaped body can be done easily and quickly, and without rotating the two components relative to each other.

When the medical instrument designed in this way is to be inserted and positioned, the bell-shaped element can first be displaced in the proximal direction to the end of the rod-shaped body, such that the bell-shaped element does not block the operator's view during insertion of the distal end section of the rod-shaped body into the uterus. The operator can insert the distal end section of the rod-shaped body quickly and safely through the vagina into the uterus, and the position of the distal end section of the rod-shaped body can be better seen by the operator and can be corrected. The risk of the distal end section of the rod-shaped body damaging the tissue of the uterus is thus greatly reduced. The bell-shaped element can be inserted into the vagina, by simple sliding displacement in the distal direction along the rod-shaped body, until it encloses the mouth of the uterus. With the instrument positioned in this way, the uterus can be manipulated by the operator, with the end section inserted in the uterus.

The insertion and positioning of the instrument according to the invention can thus be performed simply and quickly, which contributes to a marked reduction in the duration of the operation. Moreover, with the instrument designed in this way, this procedure can be carried out with far less risk of injury to the patient.

In one embodiment of the invention, the bell-shaped element can be locked by means of a locking mechanism in different axial positions on the rod-shaped body.

For example, in order to insert the rod-shaped body through the vagina into the uterus, the operator can lock the bell-shaped element in an axial position in which the bell-shaped element does not conceal the operating site. Moreover, after he has locked the bell-shaped element, the operator is able to concentrate exclusively on inserting the rod-shaped body into the uterus, without any risk of the position of the bell-shaped element on the rod changing. After the positioning, the bell-shaped element can be moved to another axial position, for example a more distal position, and locked there again.

In a further embodiment of the invention, the locking mechanism has a locking element which is arranged on the bell-shaped element and which, in the different axial positions, engages in a locking site on the rod-shaped body.

This measure has the advantage that a locking mechanism designed in this way is particularly easy to operate, since the locking element arranged on the displaceable bell-shaped element can be easily gripped, and thus easily actuated, by the operator, who displaces the bell-shaped element along the rod-shaped body. This also contributes to rapid and reliable handling of the instrument according to the invention.

In a further embodiment of the invention, a first locking site is arranged at a proximal end of the rod-shaped body.

This has the advantage that, during the insertion of the distal end section of the rod-shaped body through the vagina into the uterus, the bell-shaped element can initially be locked at the proximal end of the rod-shaped body. In this axial position, the bell-shaped element interferes least with this insertion.

In a further embodiment of the invention, a second locking site is arranged at the distal end section of the rod-shaped body.

This measure has the advantage that the bell-shaped element can be locked in a position in which it already encloses the mouth of the uterus. This is advantageous for the operator, since he does not himself have to hold the bell-shaped element in this position. With the instrument positioned in this way in the body of the patient, he is therefore able to manipulate the uterus by moving the rod-shaped body, without the risk of the bell-shaped element changing its position within the body of the patient. This places less strain on the patient, since the bell-shaped element located in the vagina does not have to be fixed in this position with the aid of additional equipment, which would be unpleasant for the patient.

In a further embodiment of the invention, the locking element locks automatically into the locking sites.

The advantage of this is that the locking element engages automatically in the locking site, which engagement can be discerned for example by the typical click heard upon locking, such that the operator knows that the locking site has been reached. The displacement in the distal direction is made easier in particular if this locking site corresponds to the position of maximum distal advance. The operator only has to displace the bell-shaped element in the distal direction until the locking mechanism engages. It is thus possible to rule out the possibility of the bell-shaped element being accidentally displaced too far in the distal direction.

In a further embodiment of the invention, the locking sites are designed as recesses in the rod-shaped body.

This measure has the advantage that the locking sites can be formed on the rod-shaped body by a simple machining procedure. The self-locking element can engage in this locking site in such a way that the operator who is holding the rod-shaped body can detect it by touch.

In a further embodiment of the invention, the locking element is designed as a spring-loaded catch.

In this way, a structurally simple locking element is made available that is pressed into the locking sites by the spring loading, such that a sufficient locking action can be obtained. Moreover, the locking element designed as a spring-loaded catch has the advantage that, with an element of this kind and with a corresponding spring force, the locking engagement can be distinctly heard and felt by the operator, particularly if the catch element and the rod-shaped body, in which the locking sites are arranged, are metal parts.

In a further embodiment of the invention, the locking mechanism has an actuating element for releasing the locking element arranged on the bell-shaped element, which actuating element is preferably designed as a push-button.

This measure has the advantage that the locking element can be disengaged from the respective locking site by simple depression of the push-button.

In a further embodiment of the invention, the bell-shaped element has a cylindrical portion at its distal end.

This measure has the advantage that the cylindrical portion of the bell-shaped element simulates the anatomical shape of the vagina, and the medical instrument can easily be inserted through the vagina. When applied to the mouth of the uterus, the latter is positioned correctly in the cylindrical portion.

In a further embodiment of the invention, the bell-shaped element is closed at its proximal end.

The bell-shaped element can be applied to the uterus so as to close the latter off in a gas-tight manner in the proximal direction. In this way, it is possible to widen the interior of the uterus by introduction of gases in order to increase the size of the operating site.

In a further embodiment of the invention, distally projecting fixing elements are arranged on the bell-shaped element.

This has the advantage that the distally projecting fixing elements fix the bell-shaped element on the mouth of the uterus. This ensures that the bell-shaped element itself firmly encloses the mouth of the uterus during manipulation of the uterus or during the entire surgical intervention.

In a further embodiment of the invention, the fixing elements are designed as pins.

This measure has the advantage that the fixing elements designed as pins penetrate relatively atraumatically into the tissue in the area of the mouth of the uterus and thus ensure a stable fit of the bell-shaped element during the entire surgical intervention.

In a further embodiment of the invention, the fixing elements protrude from an inner face of the bell-shaped element.

Such an arrangement of the fixing elements ensures that the mouth of the uterus protruding into the bell-shaped element is fixed particularly securely.

In a further embodiment of the invention, the bell-shaped element is made of ceramic.

Making the bell-shaped element from ceramic has the advantage that the insulating ceramic is useful in surgical interventions using HF instruments, which are used for high-frequency coagulation or for high-frequency cutting. High-frequency coagulation is used to surgically destroy tissue regions, to arrest bleeding, to remove tissue areas or to permit thermal coagulation of tumours. High-frequency cutting is used, for example, for removing cysts, for cutting through vessels, or for similar surgical interventions. The HF instruments are often used in surgical interventions performed on the uterus, for example in hysterectomy procedures.

In another preferred embodiment of the invention, the rod-shaped body is bent at the distal end section.

This measure has the advantage that the components, for example the bell-shaped element, when they are displaced in the proximal direction, come to lie outside the longitudinal axis of said portion. In this way, the operator has a clear view along the direction of insertion when introducing the distal end of the rod-shaped body through the vagina into the cervix.

In a further embodiment of the invention, the bell-shaped element is displaceable along the rod-shaped body on rollers.

This measure has the advantage that the bell-shaped element can be moved along the rod-shaped body without jamming.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

The invention is described and explained in greater detail below on the basis of a selected illustrative embodiment and by reference to the attached drawings, in which:

FIG. 5 shows a transverse section through the instrument according to the invention in the area of the locking mechanism, with a locking element engaging in a locking site;

FIG. 6 shows a view comparable to FIG. 5, in which the locking element is disengaged from the locking site;

DETAILED DESCRIPTION OF A PREFERRED EMBODIMENT

Figure 1:
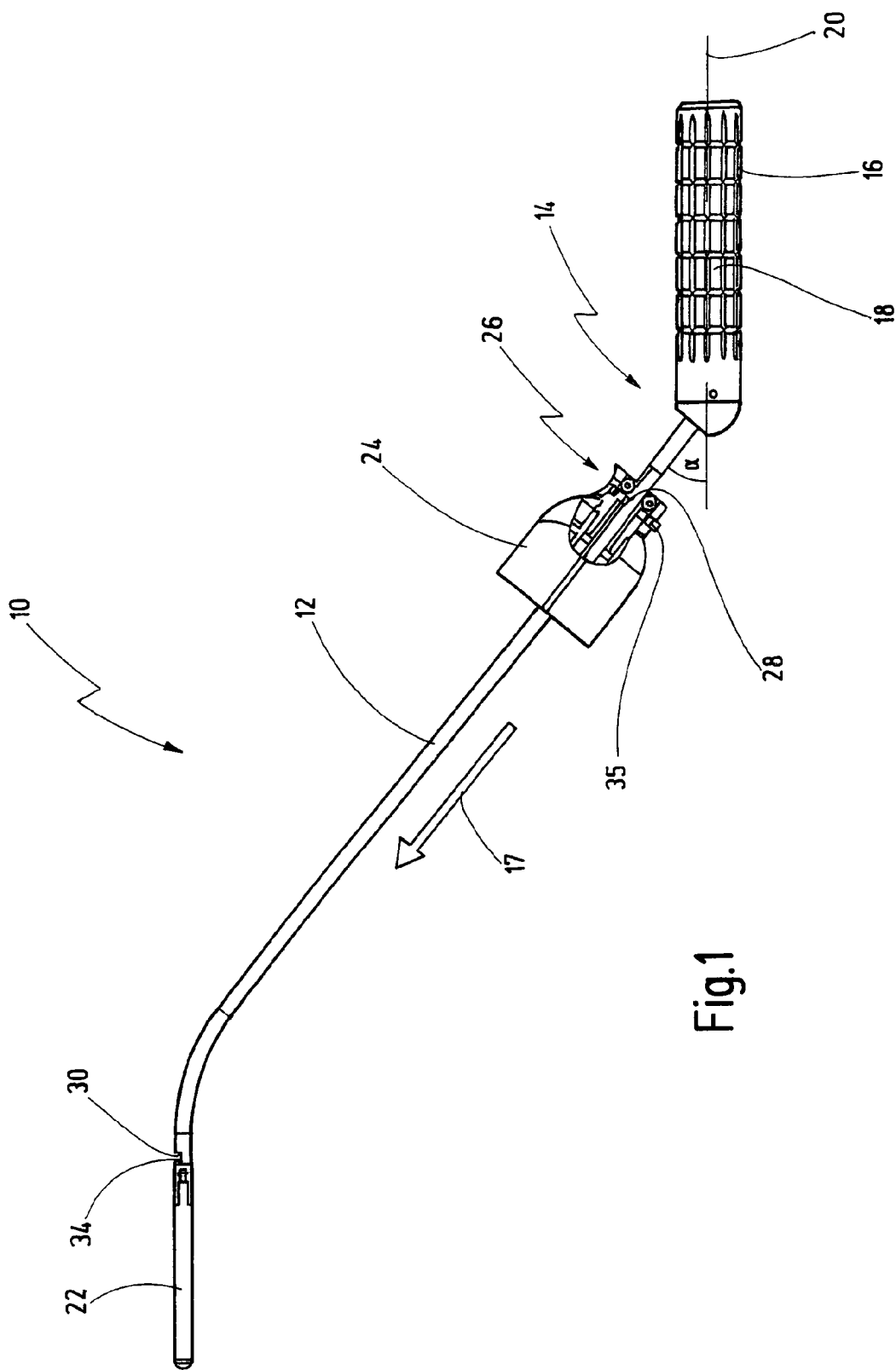
FIG. 1 shows a partly sectional side view of an instrument according to the invention, with a bell-shaped element locked in its first locking site.

A medical instrument shown in FIG. 1, and used for manipulation of an uterus, is designated in its entirety by reference number 10.

The medical instrument 10 according to the invention has a rod-shaped body 12. A handle 16 is arranged at a proximal end 14 of the rod-shaped body 12. A notched pattern 18 is cut into an outer face of the handle 16, such that the medical instrument 10 can be gripped firmly and securely by a human hand in the area of the handle 16.

The rod-shaped body 12 is connected to the handle 16 in such a way that the rod-shaped body 12 forms an angle α of ca. 45° with respect to a longitudinal axis 20 of the handle 16.

A distal rectilinear portion 22 of the rod-shaped body 12 is bent out from the longitudinal axis of the rod-shaped body 12, specifically in such a way that the distal end section 22 of the rod-shaped body 12 and the handle 16 are arranged parallel to each other.

A bell-shaped element 24 is arranged on the rod-shaped body 12, the design of which bell-shaped element 24 will be described in greater detail below in connection with FIG. 3. The bell-shaped element 24 is arranged displaceably on the rod-shaped body 12. Thus, the bell-shaped element 24 can be displaced to and fro along the rod-shaped body 12.

Moreover, the medical instrument 10 has a locking mechanism 26 by means of which the bell-shaped element 24 can be locked in different axial positions on the rod-shaped body 12, as will be described in greater detail below in connection with FIGS. 3 to 6.

In the view shown in FIG. 1, the bell-shaped element 24 is locked in a first locking site 28. The first locking site 28 is arranged at the proximal end 14 of the rod-shaped body 12. This view also depicts a second locking site 30, which is arranged at the distal end section 22 of the rod-shaped body. The two locking sites 28, 30 are designed as recesses 32, 34 in the rod-shaped body 12.

Figure 2:
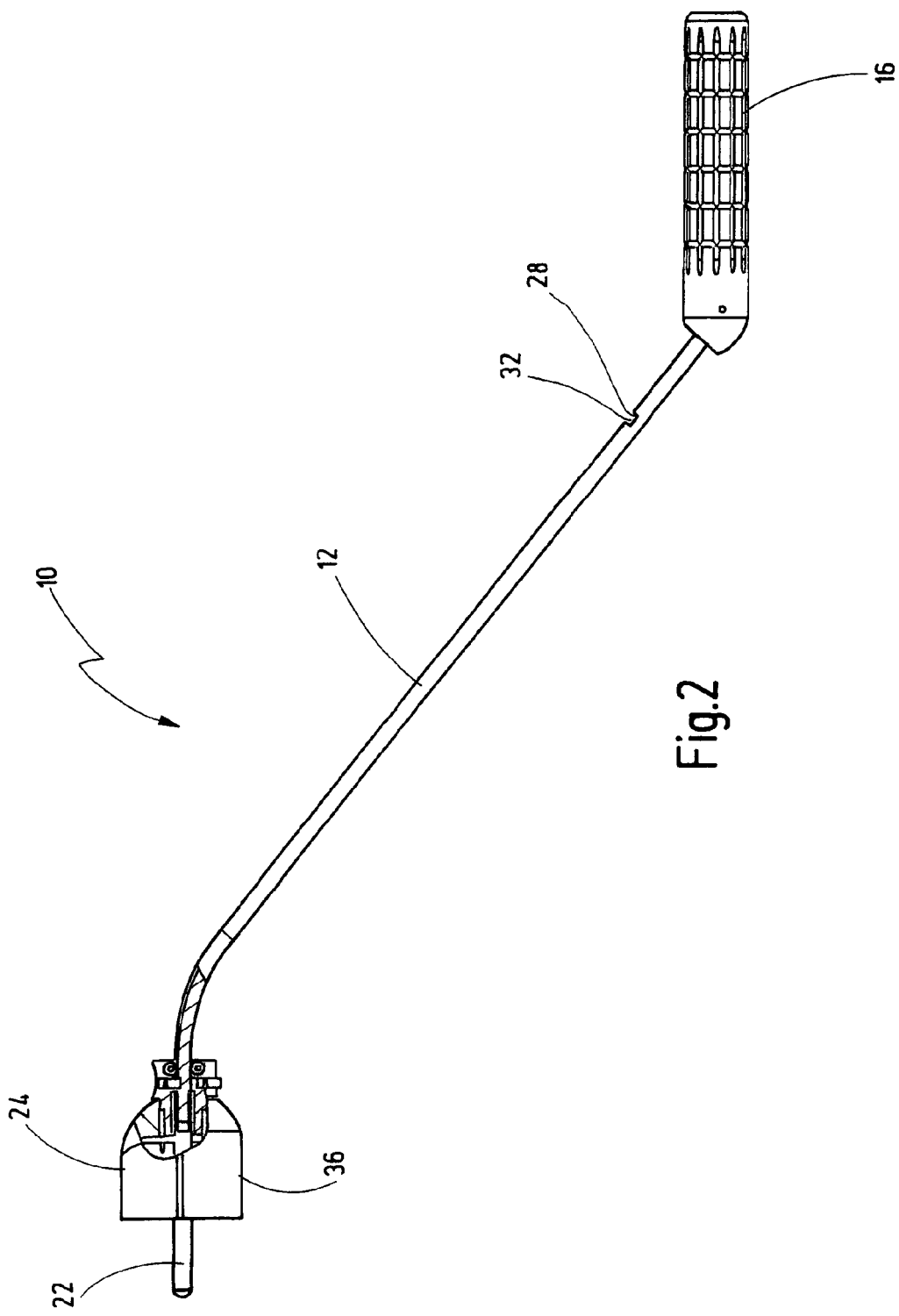
FIG. 2 shows a view comparable to the view in FIG. 1, with the bell-shaped element locked in a second locking site.

In order to bring the bell-shaped element 24 from the first locking site 28 to the second locking site 30, an actuating element 35 for releasing the locking mechanism first has to be actuated, as will be described in greater detail below in connection with FIGS. 3 to 6. Thereafter, the operator displaces the bell-shaped element 24 distally (see arrow 17) along the rod-shaped body 12, specifically until the bell-shaped element 24 is locked by means of the locking mechanism 26 in the second locking site 30, which is arranged at the distal end section 22 of the rod-shaped body 12. Such a situation is shown in FIG. 2. The distal end portion 22 protrudes from the distal end of the bell-shaped element 24.

Figure 3:
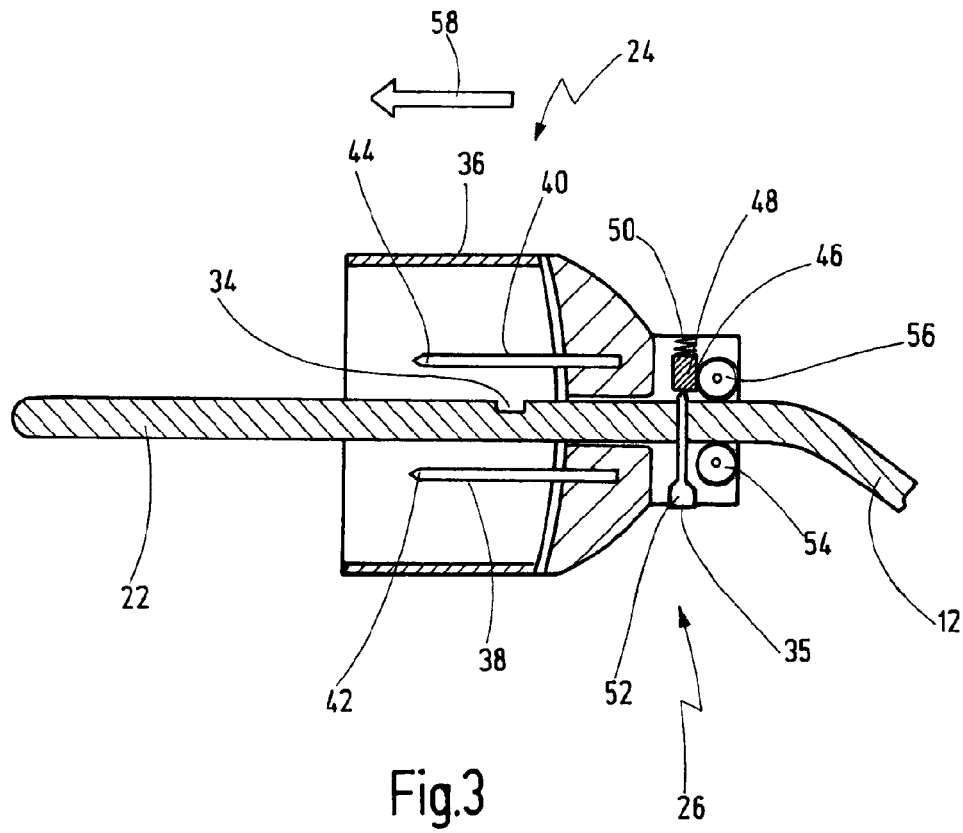
FIG. 3 shows a longitudinal section in an area of the bell-shaped element, with the bell-shaped element located just before a locking site.
Figure 4:
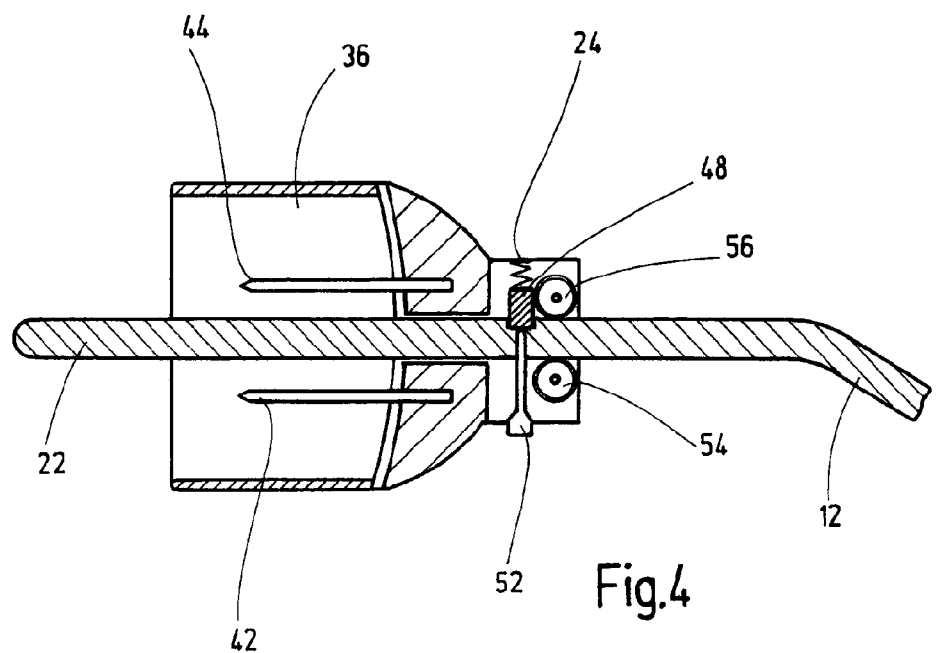
FIG. 4 shows a view comparable to the view in FIG. 3, with the bell-shaped element locked in the locking site.

The enlarged view in FIGS. 3 and 4 shows the design of the bell-shaped element 24, which is made of ceramic in this illustrative embodiment.

The bell-shaped element 24 has a cylindrical portion 36 at its distal end. Moreover, the bell-shaped element 24 is closed at its proximal end. This means that when the bell-shaped element 24 encloses the mouth of the uterus, no gases or fluids can escape from the interior of the uterus.

FIGS. 3 and 4 show two of four distally protruding fixing elements 38, 40, which are arranged in the interior of the bell-shaped element 24. In this illustrative embodiment, the fixing elements 38, 40 are designed as pins 42, 44. The fixing elements 38, 40 serve to fix the bell-shaped element 24 on the mouth of the uterus, since the fixing elements 38, 40 designed as pins 42, 44 penetrate into the tissue in the area of the mouth of the uterus, as is described in greater detail below in connection with FIGS. 7 and 8.

Two rollers 54 and 56 are also arranged opposite each other in the bell-shaped element 24, with the rod-shaped body 12 lying between them. The rollers 54, 56 serve to guide the bell-shaped element 24 along the rod-shaped body 12 during displacement.

The locking mechanism 26 can also be seen from the enlarged sectional side views in FIGS. 3 and 4.

The locking mechanism 26 has a locking element 46 which, in this illustrative embodiment, is designed as a spring-loaded catch 48. The spring-loaded catch 48 is mounted on an inner wall of the bell-shaped element 24 by means of a pretensioned spring 50.

Moreover, the locking mechanism 26 comprises the above-mentioned actuating element 35 for release of the catch 48. The actuating element 35 is designed in such a way that, as will be described in greater detail below in connection with FIGS. 5 and 6, it is permanently in contact with the spring-loaded catch 48. In this illustrative embodiment, the actuating element 35 has a push-button 52.

FIG. 3 shows a situation in which the locking element 46 designed as a spring-loaded catch 48 is not yet locked in the second locking site 30. In this situation, the spring-loaded catch 48 slides along the rod-shaped body 12. The operator pushes the bell-shaped element 24 in a direction indicated by an arrow 58 until the spring-loaded catch 48 engages in the second locking site 30 designed as a recess 34 and is locked in the latter. Such a situation is shown in FIG. 4.

With the locking mechanism 26 designed in this way, the operator does not have to concentrate exactly on the displacement of the bell-shaped element 24, because the locking element 46 locks into place automatically. The operator can hear quite distinctly when the locking element 46 locks into place in one of the locking sites 28, 30.

From the transverse section through the bell-shaped element 24 shown in FIGS. 5 and 6, it will be seen that the locking element 46 designed as a spring-loaded catch 48 has, at its end directed toward the rod-shaped body 12, a projection 60 that engages in the locking sites 28, 30 designed as recesses 32, 34. The projection 60 projects from two bearing sites 62, 64. The shape of the projection 60 is adapted to the shape of the recesses 32, 34.

The actuating element 35, lying diametrically opposite the locking element 46, has two legs 66, 68, which are in permanent contact with the bearing sites 62, 64 of the locking element 46.

In FIG. 5, the locking element 46 is locked in the second locking site 30, and the actuating element 35 is in a non-actuated state. In order to disengage the locking element 46 from the second locking site 30, the operator depresses the push-button 52. The direction is indicated by an arrow 70. When the push-button 52 is depressed, the legs 66, 68 exert a force on the bearing sites 62, 64 of the locking element 46, said force being directed counter to the spring force of the spring 50. This is sufficient to push the projection 60 out of the recess 34.

Such a situation is shown in FIG. 6. In this state, the bell-shaped element 24 can easily be displaced to and fro along the rod-shaped body 12. In doing so, it is guided by the rollers 54 and 56.

Figure 7:
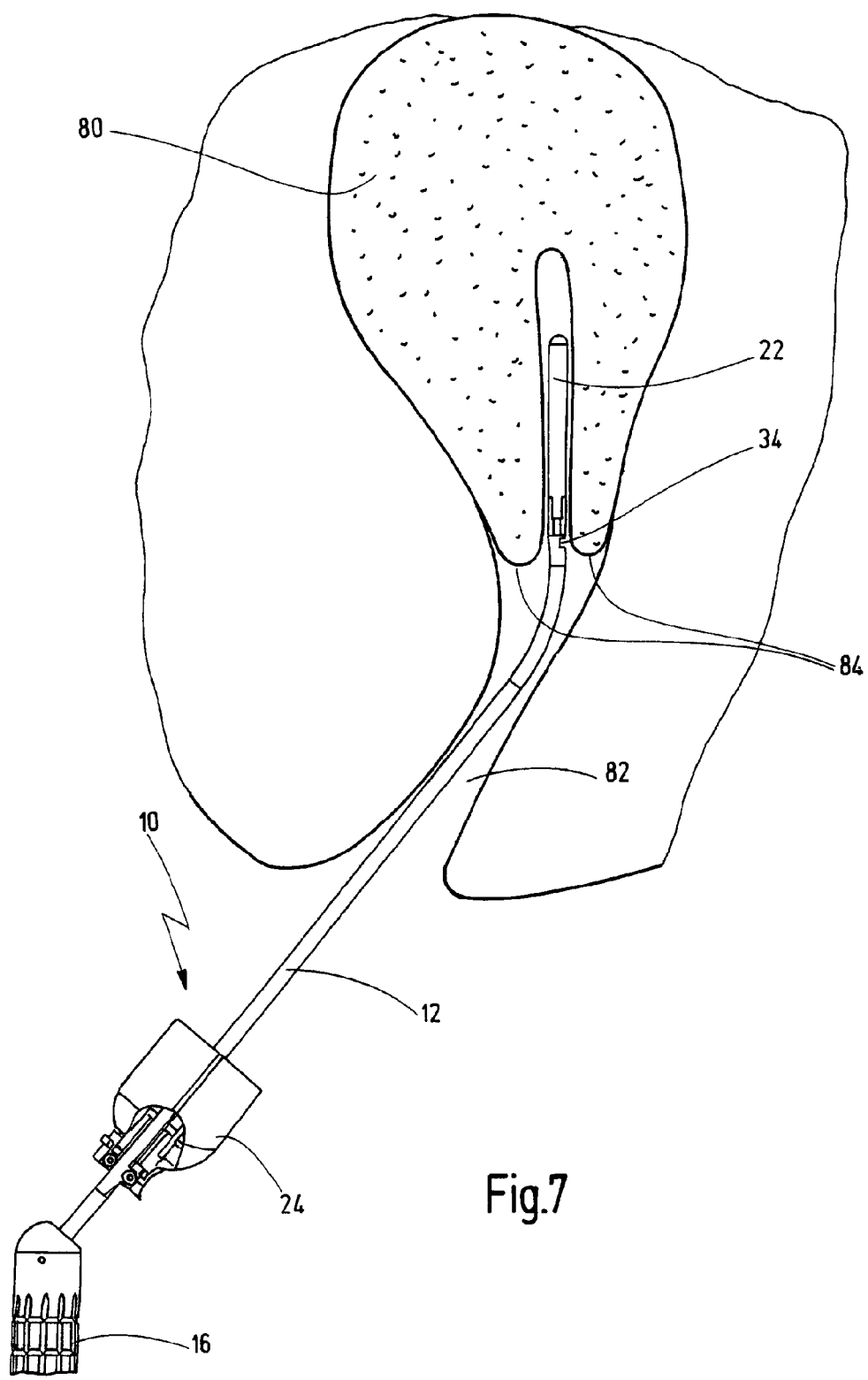
FIG. 7 shows a situation during the positioning of the medical instrument in an uterus, with a distal end section of a rod-shaped body inserted into the uterus.

The use of the instrument 10 according to the invention will be explained briefly with reference to FIGS. 7 and 8.

First, the bell-shaped element 24 is locked in the first locking site 28, which is situated at the proximal end 14 of the rod-shaped body 12. The operator then grips the handle 16 in one hand, and the distal end section 22 is inserted through the vagina 82 into the uterus 80. Such a situation is shown in FIG. 7.

In order to displace the bell-shaped element 24, locked in the first locking site 28, along the rod-shaped body 12, the push-button 52 is depressed so as to disengage the projection 60 of the locking element 46 from the locking site 28, as is shown in FIGS. 5 and 6.

The operator then moves the bell-shaped element 24 in the distal direction along the rod-shaped body 12. He inserts the bell-shaped element 24 into the vagina 82 until he hears a click. This guarantees that the locking element 46 is locked in the second locking site 30, which is arranged at the distal end section 22. In this state, the cylindrical portion 36 of the bell-shaped element 24 encloses the mouth 84 of the uterus. With the mouth 84 of the uterus enclosed, the fixing elements 38, 40 designed as pins 42, 44 penetrate into the tissue. The bell-shaped element 24 is thus fixed in this position.

Figure 8:
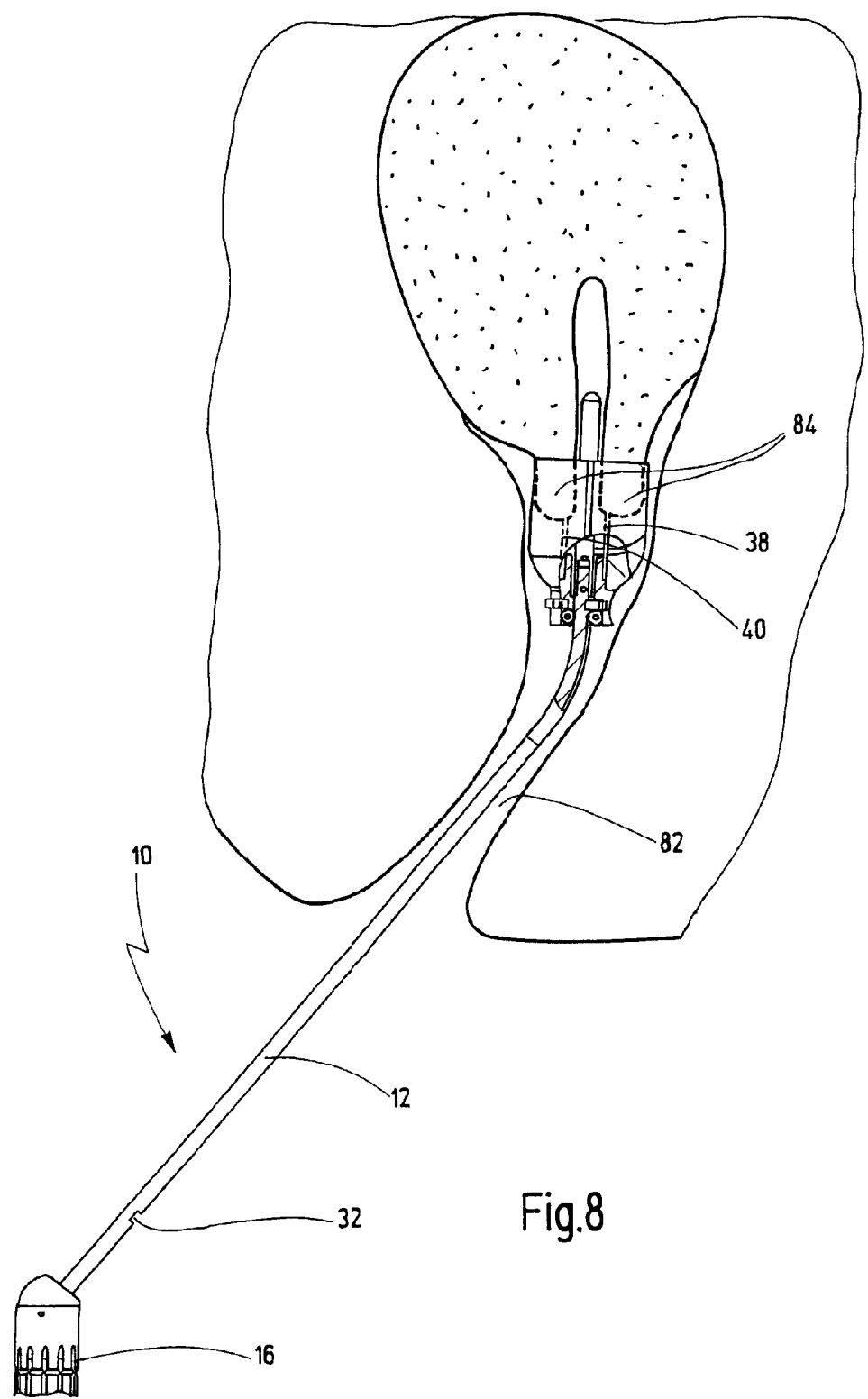
FIG. 8 shows a view comparable to FIG. 7, with the bell-shaped element enclosing the mouth of the uterus.

Such a situation is shown in FIG. 8. In this state, the uterus 80 is tightly closed off from the outside by the bell-shaped element 24.

Depending on the intervention, the device 10 can be removed together with the cervical tissue detached from the body and adhering to the bell-shaped element 24. If only an examination is to be performed, the instrument 10 is withdrawn again.

What is claimed is:

1. A medical instrument, comprising a rod-shaped body having a distal end section, said distal end section can be inserted through a vagina into an uterus, a bell-shaped element mounted on said rod-shaped body, said bell-shaped element being slidingly displaceable along said rod-shaped body at least between a first axial position on said rod-shaped body close to a proximal end of said rod-shaped body and up to a subsequent axial position at said distal end portion inserted into a uterus, a sliding displacement of said bell-shaped element being without rotating said rod-shaped body and said bell-shaped element relative to each other;

wherein said bell-shaped element can be locked by means of a locking mechanism in different axial positions on said rod-shaped body, said locking mechanism locks said bell-shaped element against a displacement of said bell-shaped element along said rod-shaped body, wherein said locking mechanism has a locking element being arranged on said bell-shaped element, said locking element, in said different axial positions, engages in a locking site on said rod-shaped body, and wherein a first locking site is arranged at a proximal end portion of said rod-shaped body and a second locking site is arranged at said distal end portion of said rod-shaped body.

2. The medical instrument of claim 1, wherein said locking element locks automatically into said locking sites.

3. The medical instrument of claim 1, wherein said locking sites are designed as recesses in said rod-shaped body.

4. The medical instrument of claim 1, wherein said locking element is designed as a spring-loaded catch.

5. The medical instrument of claim 1, wherein said locking mechanism has an actuating element for releasing said locking element arranged on said bell-shaped element.

6. The medical instrument of claim 5, wherein said actuating element is a push-button.

7. The medical instrument of claim 1, wherein said bell-shaped element has a cylindrical portion at a distal end thereof.

8. The medical instrument of claim 1, wherein said bell-shaped element is closed at its proximal end.

9. The medical instrument of claim 1, wherein distally projecting fixing elements are arranged on said bell-shaped element.

10. The medical instrument of claim 9, wherein said fixing elements are designed as pins.

11. The medical instrument of claim 10, wherein said pins protrude from an inner phase of said bell-shaped element.

12. The medical instrument of claim 1, wherein said bell-shaped element is made of a ceramic material.

13. The medical instrument of claim 1, wherein said rod-shaped body is bent at said distal end section.

14. The medical instrument of claim 1, wherein said bell-shaped element is provided with rollers via which said bell-shaped element can be slidingly displaced along said rod-shaped body.

* * * * *